June 11, 1957 E. S. BOERNER Plant Pat. 1,610
CHRYSANTHEMUM PLANT
Filed Oct. 26, 1956
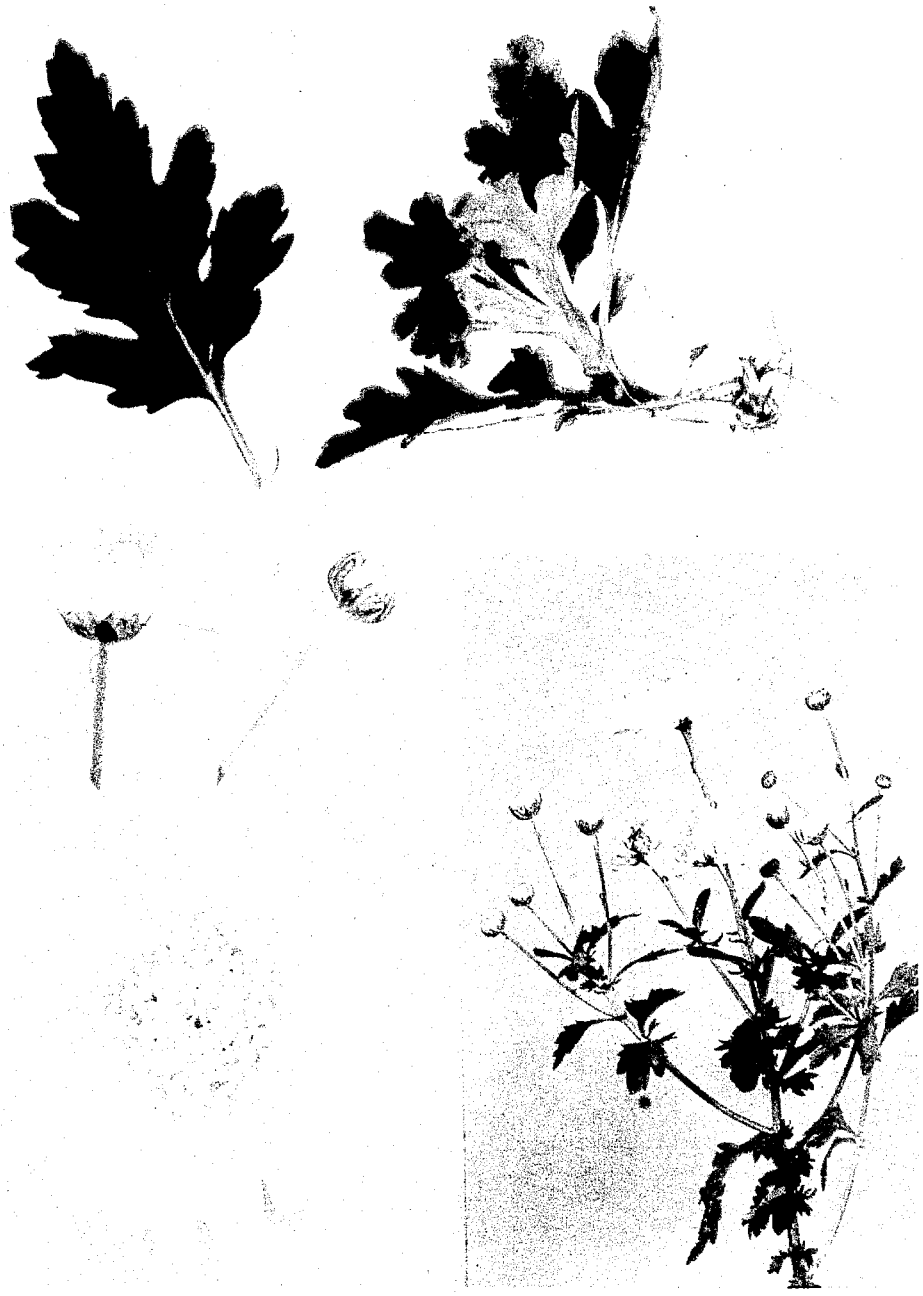
Inventor.
E. S. Boerner
By: Robert Robb
Attorneys.

United States Patent Office

Plant Pat. 1,610
Patented June 11, 1957

1,610

CHRYSANTHEMUM PLANT

Eugene S. Boerner, Newark, N. Y., assignor to Jackson & Perkins Company, Newark, N. Y., a corporation of New York Application October 26, 1956, Serial No. 618,664

1 Claim. (Cl. 47—60)

The present invention relates to a new and distinct variety of chrysanthemum plant of the decorative type, which was originated by me by crossing the variety "Thrush" (Plant Patent No. 1,168) with the variety "Sea Gull" (Plant Patent No. 1,130).

The primary objective of this breeding was to produce a new chrysanthemum variety having a plant size substantially corresponding to that of the parent variety "Sea Gull," but which has the vigor of growth and bears flowers of a color substantially corresponding to those of the parent variety "Thrush." This objective was fully achieved, along with other improvements, as evidenced by the following characteristics which are outstanding in my new variety:

(1) A good plant size corresponding to that of "Sea Gull";

(2) Stiff and upright growth, with the vigor of "Thrush";

(3) A silvery appearance of the foliage;

(4) Very double form of the flowers; and (5) A distinctive general color tonality corresponding to White, lightly overcast with Seashell Pink, like that of "Thrush."

The foregoing characteristics and distinctions definitely differentiate my new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character, and also shows a typical specimen plant, in black-and-white, which is illustrative of the form and habit of growth of the plant.

The following is a detailed description of my new variety, with color terminology in accordance with Ridgway's Color Standards and Nomenclature:

Parentage: "Thrush" × "Sea Gull."

Classification: Decorative.

Growth: From 2½ to 3 feet tall.

Cold resistance: Winter hardy in northern New York, and flowers are very frost resistant.

Blooming period: In the Newark, New York, climatic area, blooming usually begins about September 15th and continues to heavy frosts.

*Flower*

(Observations made from specimens grown in a field at Newark, New York, about the middle of September.)

Bud:

*Color.*—When sepals first divide—Pale Cinnamon Pink, Plate 29. When petals begin to unfurl—Pale Pinkish Cinnamon, Plate 29, lightly overcast with White, Plate 53. When half-blown: inside of petals—White, Plate 53, lightly overcast with Pale Pinkish Cinnamon, Plate 29; reverse of petals—White, Plate 53.

*Peduncle.*—Color: Biscay Green, Plate 17. Strength: strong.

Bloom:

*Size.*—From 4½ to 5 inches.

*Stem.*—Long; heavy.

*Form.*—Decorative.

*Petalage.*—Very double.

*Color.*—Center of flower—Marguerite Yellow, Plate 30, lightly overcast with Pale Flesh Color, Plate 14. Outer petals—White, Plate 53. Base of petals—Light Dull Green Yellow, Plate 17. Inside of petals—White, Plate 53, lightly overcast with Seashell Pink, Plate 14. Reverse of petals—White, Plate 53.

*Petals.*—Texture—medium. Form—large; with slightly wavy ends.

*Fragrance.*—Characteristic chrysanthemum.

*Plant*

Form: Upright; stiff.

Growth: Medium; vigorous.

Foliage:

*Size.*—Medium large.

*Quantity.*—Normal.

*Color.*—Upper side—Dark Dull Yellow-Green, Plate 32. Reverse side—Light Elm Green, Plate 17.

*Texture.*—Leathery; displays a silvery sheen.

I claim:

A new and distinct variety of chrysanthemum plant of the decorative type, substantially as herein shown and described, characterized particularly as to novelty by its good plant size and vigor, its stiff upright growth, the silvery appearance of its foliage, the very double form of its flowers, and the distinctive White, lightly overcast with Seashell Pink, general color tonality of its flowers.

No references cited.